(12) United States Patent
Bédard (10) Patent No.: US 7,137,998 B2
(45) Date of Patent: *Nov. 21, 2006

(54) POSITIONING OF LOWER EXTREMITIES ARTIFICIAL PROPRIOCEPTORS

(76) Inventor: Stéphane Bédard, 256, rue du Tonnelier, Saint-Augustin-de-Desmaures (Québec) (CA) G3A 2K5

( * ) Notice: Subject to any disclaimer, the term of this patent is extended or adjusted under 35 U.S.C. 154(b) by 249 days.

This patent is subject to a terminal disclaimer.

(21) Appl. No.: 10/627,503

(22) Filed: Jul. 25, 2003

(65) Prior Publication Data

US 2004/0088057 A1 May 6, 2004

Related U.S. Application Data

(60) Provisional application No. 60/405,281, filed on Aug. 22, 2002.

(51) Int. Cl.
  *A61F 2/72* (2006.01)
  *A61F 2/70* (2006.01)
  *A61F 2/64* (2006.01)
(52) U.S. Cl. .............................. 623/25; 623/24; 623/44
(58) Field of Classification Search .................. 623/24, 623/25, 43, 44
  See application file for complete search history.

(56) References Cited

U.S. PATENT DOCUMENTS

| 4,558,704 | A | 12/1985 | Petrofsky |
|---|---|---|---|
| 5,062,856 | A | 11/1991 | Sawamura et al. |
| 5,383,939 | A | 1/1995 | James |
| 5,571,205 | A | 11/1996 | James |
| 5,779,735 | A | 7/1998 | Molino |
| 5,888,212 | A | 3/1999 | Petrofsky et al. |
| 5,893,891 | A | 4/1999 | Zahedi |
| 6,113,642 | A | 9/2000 | Petrofsky et al. |
| 2002/0052663 | A1 | 5/2002 | Herr et al. |
| 2002/0198604 | A1 * | 12/2002 | Schulman et al. ............ 623/25 |

FOREIGN PATENT DOCUMENTS

| DE | 42 29 330 A1 * | 3/1994 |
|---|---|---|
| FR | 2 293 185 | 7/1976 |
| FR | 2623086 | 5/1989 |
| GB | 2 201 260 | 8/1988 |
| GB | 2 302 949 A * | 2/1997 |
| WO | WO 96/41599 | 12/1996 |
| WO | WO 00/38599 | 7/2000 |

OTHER PUBLICATIONS

EPO—European Search Report, Mar. 2, 2004.

\* cited by examiner

*Primary Examiner*—David H. Willse
(74) *Attorney, Agent, or Firm*—Devine, Millimet & Branch; Paul C. Remus

(57) ABSTRACT

The method is used for controlling an actuating mechanism of a prosthesis provided on one side of the lower body of an individual, the individual having a healthy leg on the other side. Accordingly, the method comprises providing a plurality of artificial proprioceptors, at least one of the artificial proprioceptors being on the side of the healthy leg, and at least one of the artificial proprioceptors being on provided with the prosthesis, generating data signals in real time at the artificial proprioceptors, and generating control signals in real time for controlling the actuating mechanism in response to the data signals.

78 Claims, 9 Drawing Sheets

POSITIONING OF LOWER EXTREMITIES ARTIFICIAL PROPRIOCEPTORS

CROSS-REFERENCE TO RELATED APPLICATION

The present application claims the benefits of U.S. provisional patent application No. 60/405,281 filed Aug. 22, 2002, which is hereby incorporated by reference.

TECHNICAL FIELD

The present invention relates to the positioning of lower extremities artificial proprioceptors for use with a control system and/or a method for controlling an actuated prosthesis. This invention is particularly well adapted for controlling an actuated leg prosthesis for above-knee amputees.

BACKGROUND

As is well known to control engineers, the automation of complex mechanical systems is not something easy to achieve. Among such systems, conventional powered artificial limbs are notorious for having control problems. These conventional prostheses are equipped with basic controllers that artificially mobilize the joints without any interaction from the amputee and are only capable of generating basic motions. Such basic controllers do not take into consideration the dynamic conditions of the working environment, regardless the fact that the prosthesis is required to generate appropriate control within a practical application. They are generally lacking in predictive control strategies necessary to anticipate the artificial limb's response as well as lacking in adaptive regulation enabling the adjustment of the control parameters to the dynamics of the prosthesis. Because human limb mobility is a complex process including voluntary, reflex and random events at the same time, conventional prostheses do not have the capability to interact simultaneously with the human body and the external environment in order to have minimal appropriate functioning.

Considering this background, it clearly appears that there was a need to provide the capability to interact simultaneously with the human body and the external environment to a control system and/or methods for controlling a dynamic prosthesis in order to fulfill the needs of amputees, in particular those of above-knee amputees.

SUMMARY

In accordance with one aspect of the present invention, there is provided a method of controlling an actuating mechanism of a prosthesis provided on one side of the lower body of an individual, the individual having a healthy leg on the other side, the method comprising:

providing a plurality of artificial proprioceptors, at least one of tile artificial proprioceptors being on the side of the healthy leg, and at least one of the artificial proprioceptors being on provided with the prosthesis;

generating data signals in real time at the artificial proprioceptors; and generating control signals in real time for controlling the actuating mechanism in response to the data signals.

In accordance with another aspect of the present invention, there is provided a device for controlling an actuating mechanism of a prosthesis provided on one side of the lower body of an individual, the individual having a healthy leg on the other side, the device comprising:

a plurality of artificial proprioceptors, at least one of the artificial proprioceptors being on the side of the healthy leg, and at least one of the artificial proprioceptors being on the side of the prosthesis;

means for generating data signals in real time at the artificial proprioceptors; and means for generating control signals in real time for controlling tile actuating mechanism in response to the data signals.

In accordance with a further aspect of the present invention, there is provided a lower extremities prosthesis provided on one side of the lower body of an individual, the individual having a healthy leg on the other side, the prosthesis comprising:

a plurality of artificial proprioceptors, at least one of the artificial proprioceptors being on the side of the healthy leg, and at least one of the artificial proprioceptors being on provided with the prosthesis;

means for generating data signals in real time at the artificial proprioceptors:

at least one actuating mechanism; and means for generating control signals in real time for controlling the actuating mechanism in response to the data signals.

These and other aspects of the present invention are described in or apparent from the following detailed description, which description is made in conjunction with the accompanying figures.

DETAILED DESCRIPTION

The appended figures show positioning of lower extremities artificial proprioceptors (20) for use with a control system (100) and a method for controlling a prosthesis (14) having an actuating mechanism (16) in accordance with the preferred embodiment of the present invention. It should be understood that the present invention is not limited to the illustrated implementation since various changes and modifications may be effected herein without departing from the scope of the appended claims.

Figure 1:
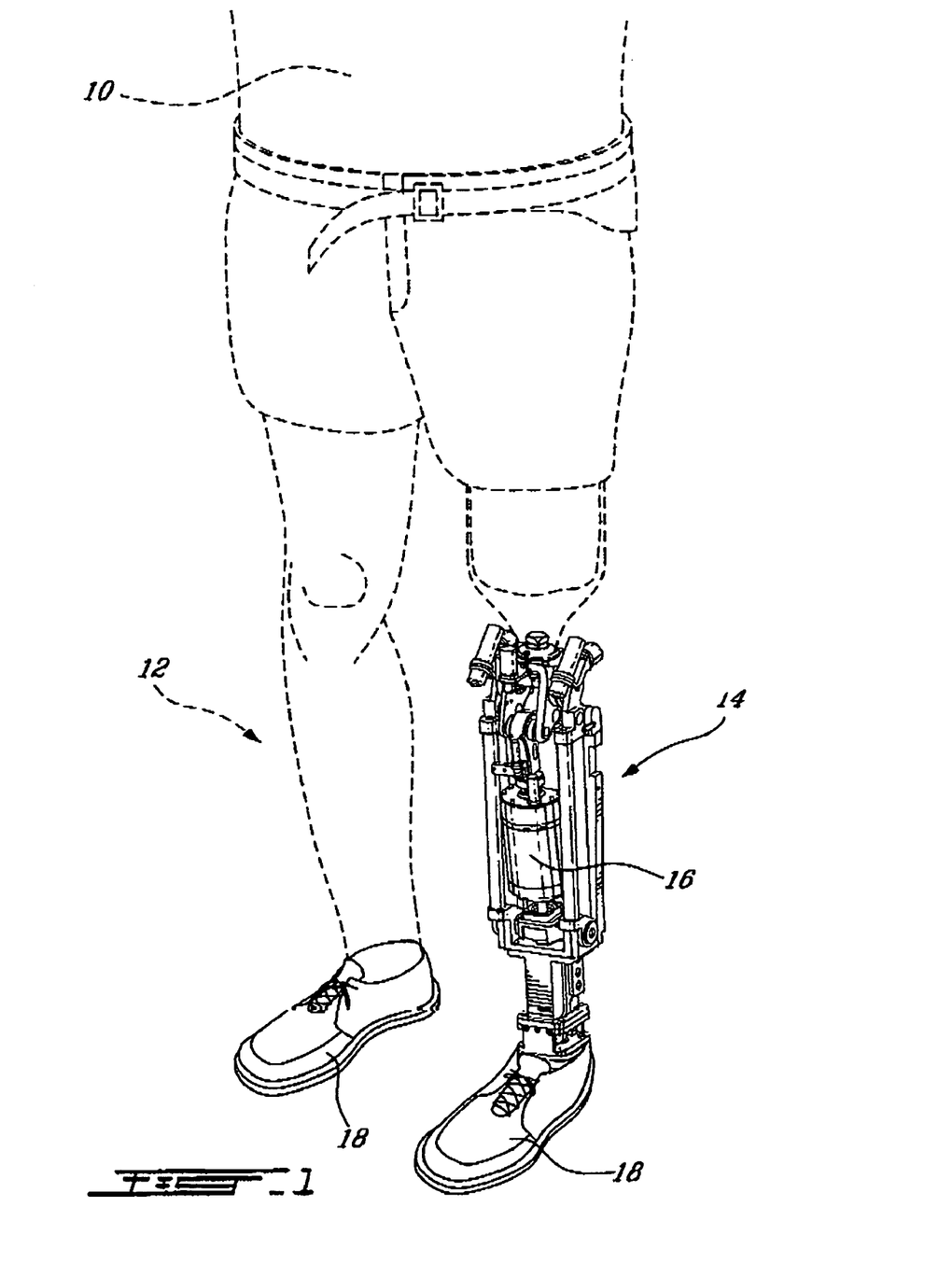
FIG. 1 shows the lower body of an individual provided with a prosthesis on one side and having a healthy leg on the other side.

FIG. 1 shows a prosthesis (14) provided on one side of the lower body of an individual (10), the individual (10) having a healthy leg (12) on the other sides. Artificial proprioceptors (20) are provided both on the healthy leg (12) and on the prosthesis (14). The prosthesis (14) comprises an actuating mechanism (16) which may be either passive or active. A passive actuating mechanism may be generally defined as an electro-mechanical component that only absorbs mechanical energy in order to modify dynamics of mechanical joints of the prosthesis, while an active actuating mechanism may be generally defined as an electro-mechanical component that absorbs and supplies mechanical energy in order to modify dynamics of mechanical joints of the prosthesis.

An example of a passive actuating mechanism is described in U.S. patent application Ser. No. 09/767,367, filed Jan. 22, 2001, entitled "ELECTRONICALLY CONTROLLED PROSTHETIC KNEE". Examples of active actuating mechanisms are described in U.S. patent application Ser. No. 10/463,495 filed Jun. 17, 2003, entitled ACTUATED PROSTHESIS FOR ABOVE-KNEE AMPUTEES", by Stéphane Bédard et al., the entire disclosure of which is hereby incorporated by reference herein.

Figure 2:
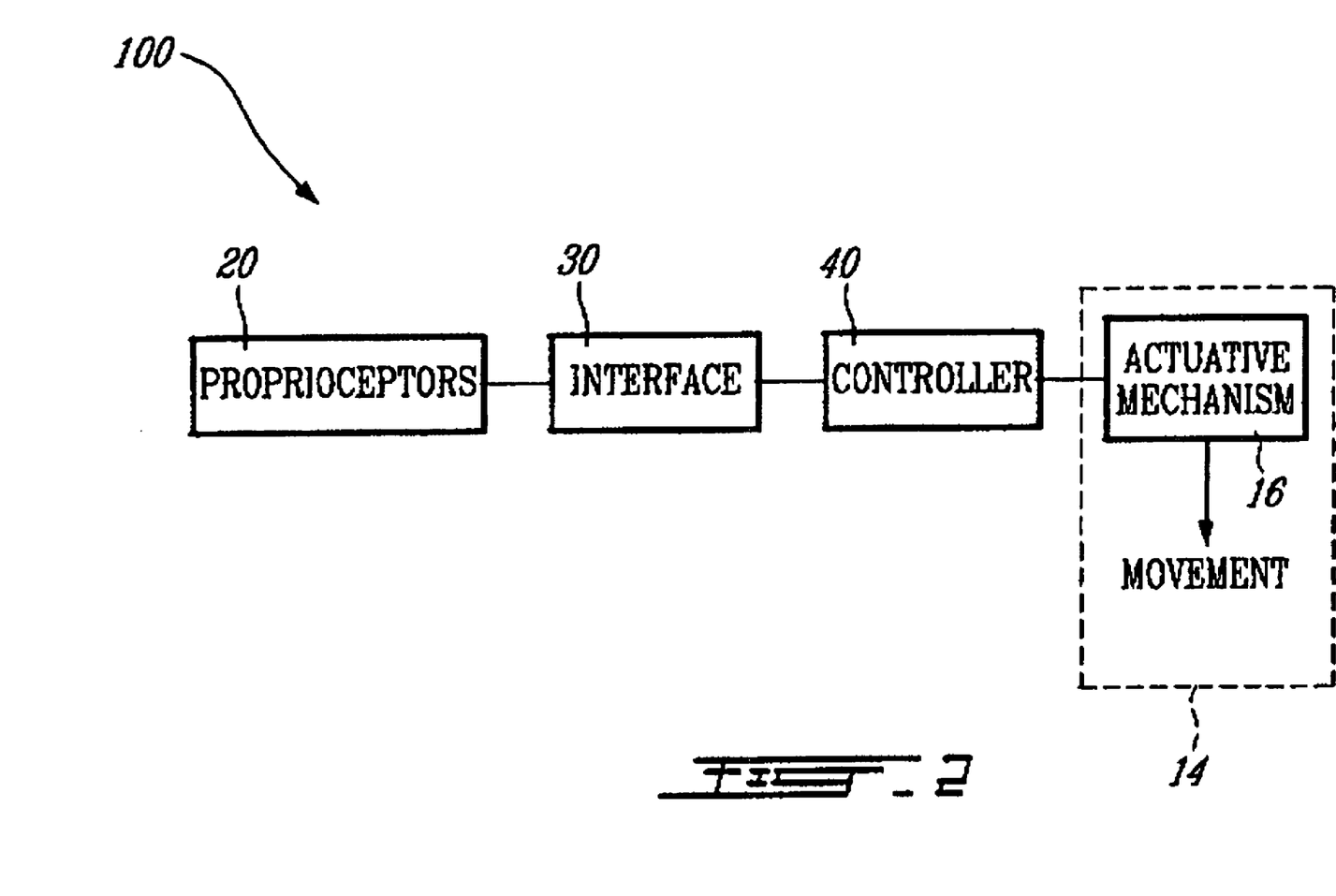
FIG. 2 is a block diagram showing a control system for a prosthesis having an actuating mechanism.

FIG. 2 shows the control system (100) being combined with artificial proprioceptors (20) and a prosthesis (14) having an actuating mechanism (16), such as shown in FIG. 1. The purpose of the control system (100) is to provide the requited signals allowing to control the actuating mechanism (16). To do so, the control system (100) is interfaced with the amputee (10) using the artificial proprioceptors (20) to ensure proper coordination between the amputee (10) and the movements of the prosthesis (14). The set of artificial proprioceptors (20) captures information, in real time, about the dynamics of the amputee's movement and provides that information to the control system (100). The control system (100) is then used to determine the resistance to be applied to a joint, in the case of a passive actuating mechanism, or the joint trajectories and the required force or torque that must be applied by a joint, in the case of an active actuating mechanism, in order to provide coordinated movements.

It should be noted that the present invention is not limited to its use with the mechanical configuration illustrated in FIG. 1. The control system (100) may be used with a leg prosthesis having more than one joint. For instance, it may be used with a prosthesis having an ankle joint, metatarsophalangeal joint or a hip joint in addition to a knee joint. Moreover, instead of a conventional socket, a osseo-integrated devices could also be used, ensuring a direct attachment between the mechanical component of the prosthesis and the amputee skeleton. Other kinds of prostheses may be used as well.

The control system (100) shown in FIG. 2 comprises an interface (30) through which data signals coming from the artificial proprioceptors (20) are received. They may be received either from an appropriate wiring or from a wireless transmission. The data signals from the artificial proprioceptors (20) provided on a healthy leg (12) are advantageously sent through the wireless transmission using an appropriate radio frequency (RF) module. Of course, other combinations of communication link technologies may be used, such as wired, wireless, optical, etc.

Software residing on a controller (40) contains all the algorithms enabling the control system (100) to provide the required signals allowing to control the actuating mechanism (16).

The artificial proprioceptors (20), located on both the healthy leg (12) and the prosthesis (14), may include myoelectric sensors, neuro-sensors, kinematic sensors, kinetic sensors or plantar pressure sensors. Myoelectric sensors are electrodes used to measure the internal or the external myoelectrical activity of skeletal muscles. Neuro-sensors are electrodes used to measure the summation of one or more action potentials of peripheral nerves. Kinematic sensors are used to measure the position of articulated joints, the mobility speed or acceleration of lower extremities. Kinetic sensors are used to measure rotational forces at the articulated joints or reaction forces of lower extremities. Plantar pressure sensors are used to measure the vertical plantar pressure of a specific underfoot area. Of course, additional types of sensors which provide information about various dynamics of human locomotion may be used. For a given application, the use of artificial proprioceptors (20) is not restricted to a specific type of sensor, multiple types of sensors in various combinations may be used.

The controller (40) ensures, in real-time, the decomposition of the locomotion of an individual (10) based on the information provided by the artificial proprioceptors (20). In accordance with the present invention, it was found that data signals received from individual artificial proprioceptors (20) located on both the healthy leg (12) and the prosthesis (14) of an individual (10) can provide enough information in order to control the actuating mechanism (16) of the prosthesis (14). For instance, in the case of plantar pressure sensors, it has been noticed experimentally that the slope (first derivative), the sign of the concavity (second derivative) and the slope of concavity (third derivative) of the data signals received from plantar pressure sensors, and of combinations of those signals, give highly accurate and stable information on the human locomotion and enable the decomposition of the human locomotion into a finite number of portions. This breakdown ensures the proper identification of the complete mobility dynamics of the lower extremities in order to model the human locomotion. Of course, the use of plantar pressure sensors is given as an example and does not limit the definition of artificial proprioceptors to such sensors.

EXAMPLE

In a sample application, the artificial proprioceptors (20) may comprise localized plantar pressure sensors, which measure the vertical plantar pressure of a specific underfoot area, combined with a pair of gyroscopes which measure the angular speed of body segments of the lower extremities and a kinematic sensor which measures the angle of the prosthesis (14) knee joint. The plantar pressure sensors are used under both feet, the foot of the healthy leg (12) as well as the foot of the prosthesis (14). One of the gyroscopes is located at the shank of the healthy leg (12) while the other is located on the upper portion of the prosthesis (14) above the knee joint, i.e. at the residual thigh. As for the kinematic sensor, it is located at the prosthesis (14) knee joint. Of course, the use of plantar pressure sensors, gyroscopes and kinematic sensors is given as an example and does not limit the definition of artificial proprioceptors to such sensors.

Figure 4:
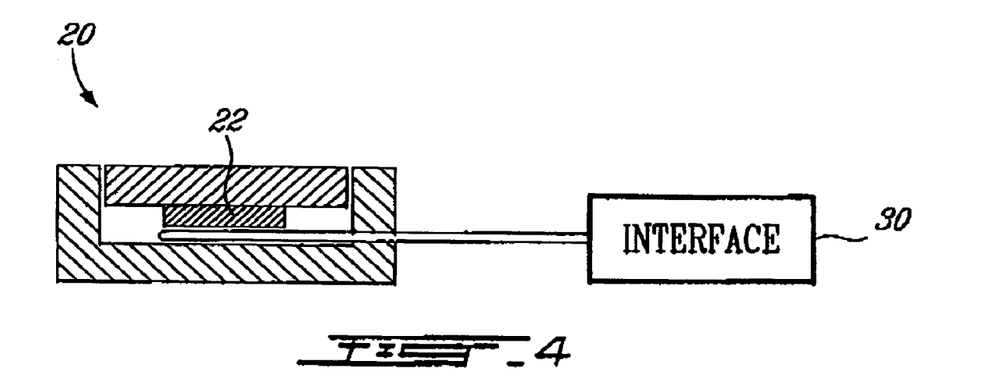
FIG. 4 is a cross sectional view of a sensor shown in FIG. 3.
Figure 5A:
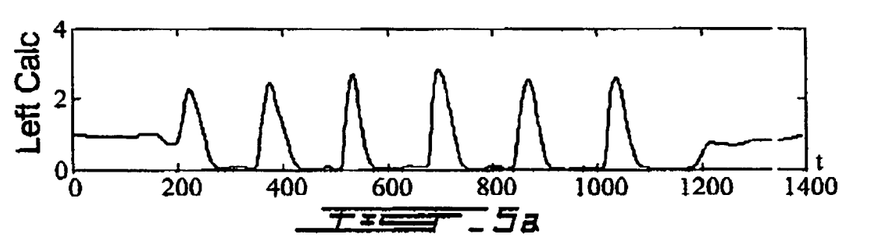
FIGS. 5a to 5d are examples of four data signals using plantar pressure sensors during typical walking on flat ground.
Figure 5B:
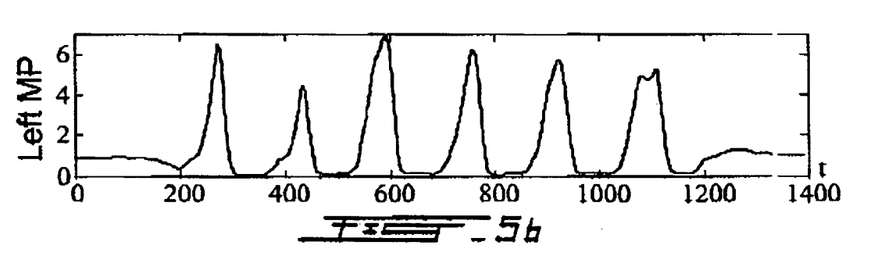
Figure 5C:
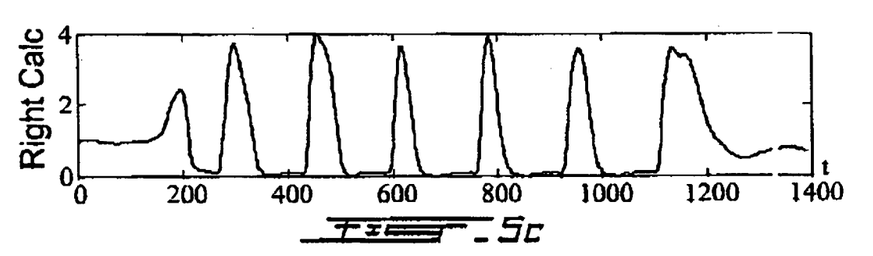

In FIG. 4, the plantar pressure sensors (20) are provided in a custom-made insole (18), preferably in the form of a standard orthopedic insole, that is modified to embed the two sensors (20) for the measurement of two localized plantar pressures. Each sensor (20), as shown in FIG. 5, is preferably composed of a thin Force-Sensing Resistor (FSR) polymer cell (22) directly connected to the interface (30) or indirectly using an intermediary system (not shown), for instance a wireless emitter The FSR cell (22) has a decreasing electrical resistance in response to an increasing force applied perpendicularly to the surface thereof. Each cell (22) outputs a time variable electrical signal for which the intensity is proportional to the total vertical plantar pressure over its surface area. The size and position of the plantar pressure sensors (20) were defined in accordance with the stability and the richness (intensity) of the localized plantar pressure signals provided by certain underfoot areas during locomotion.

Figure 3:
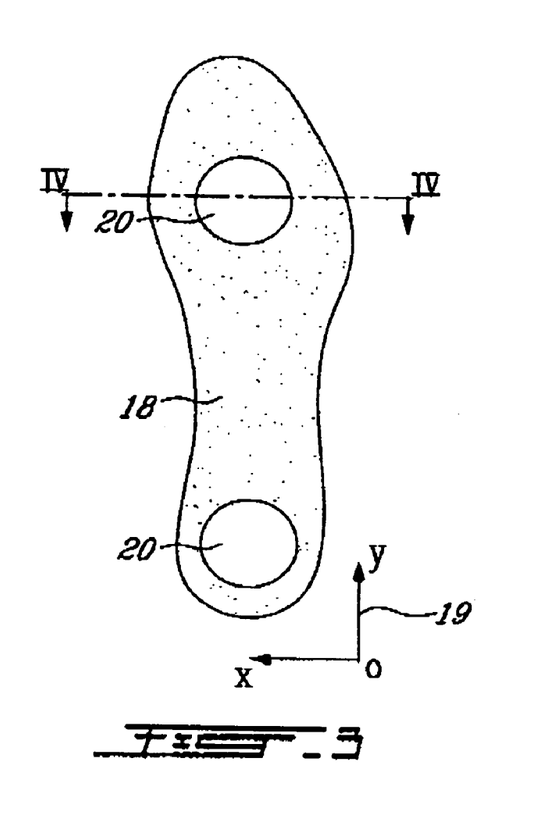
FIG. 3 is an upper schematic view of an insole provided with planter pressure sensors.

Experimentation provided numerous data concerning the spatial distribution of foot pressures and more specifically on the Plantar Pressure Maximal Variation (PPMV) during locomotion. The PPMV was defined as the maximum variation of the plantar pressure at a particular point (unnderfoot area of coordinate i,j) during locomotion. The X-Y axis (19) in FIG. 3 was used to determine the i,j coordinates of each underfoot area. It was found by experimentation that the calcaneus and the Metatarsophalangeal (MP) regions are two regions of the foot sole where the PPMV may be considered as providing a signal that is both stable and rich in information.

The normalized position of the pressure sensors and their size are shown in Table 1, where the length L and the width W are respectively the length and the width of the subject's foot. The coefficients in Table 1 have been obtained by experimentation. A typical diameter for the plantar pressure sensors (20) is between 20 and 30 mm.

TABLE 1

Normalized position and size of plantar pressure sensors

| Area | Position (X, Y) | Size (diameter) |
|---|---|---|
| Calcaneus | $(0.51 \cdot W, 0.14 \cdot L)$ | $0.29 \cdot \sqrt{L \cdot W}$ |
| MP | $(0.47 \cdot W, 0.76 \cdot L)$ | $0.24 \cdot \sqrt{L \cdot W}$ |

Figure 5D:
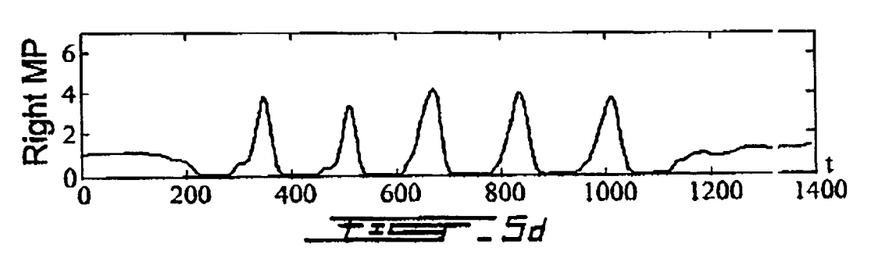
Figure 6A:
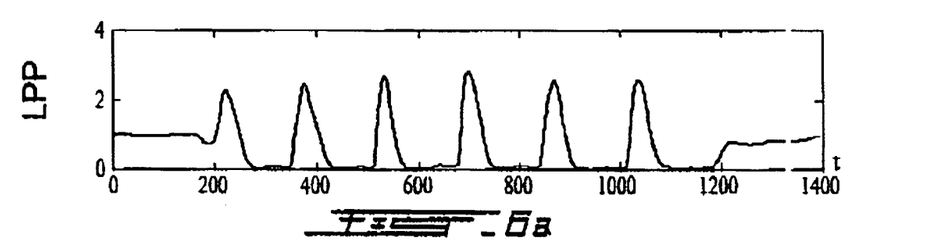
FIGS. 6a to 6d give an example of a data signal obtained from a plantar pressure sensor at the calcaneus region and its first three differentials.
Figure 6B:
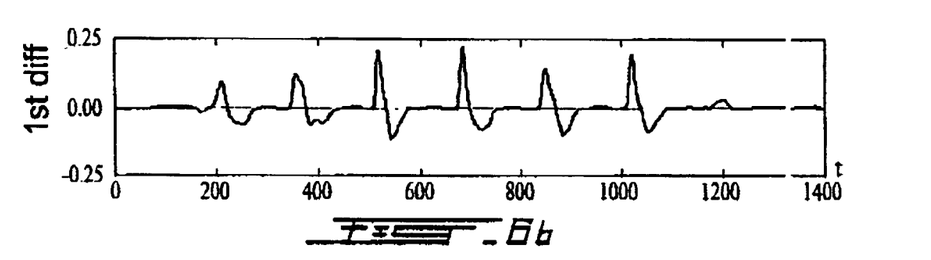
Figure 6C:
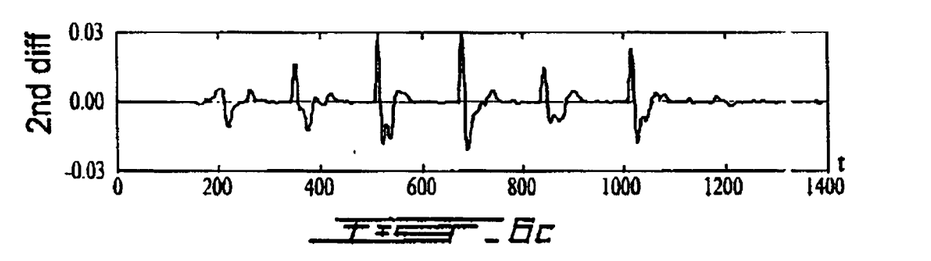
Figure 6D:
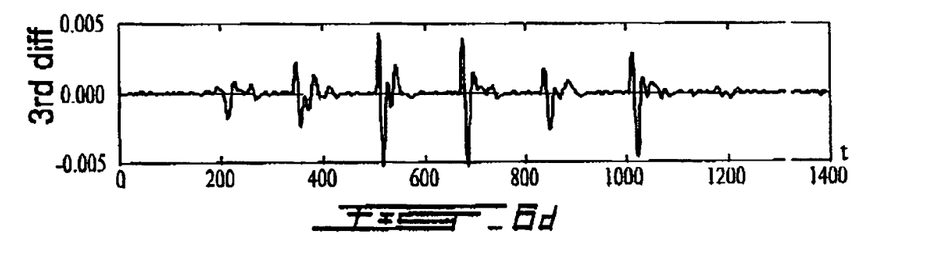
Figure 7A:
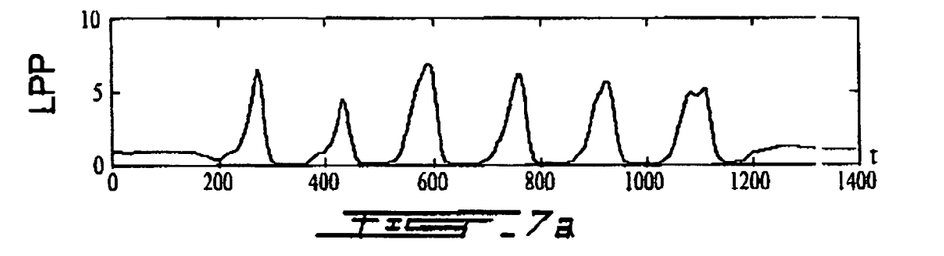
FIGS. 7a to 7d give an example of a data signal obtained from a plantar pressure sensor at the metatarsophalangeal (MP) region and its first three differentials.
Figure 7B:
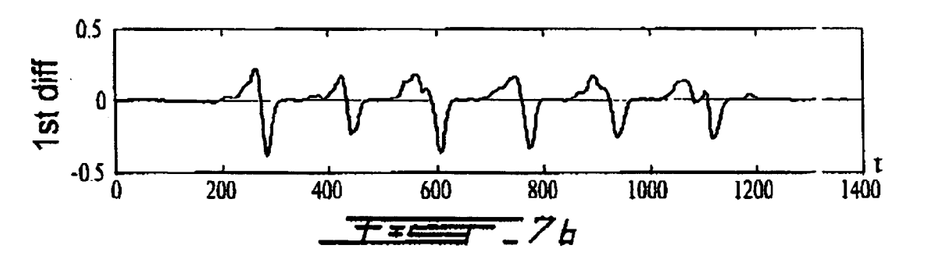
Figure 7C:
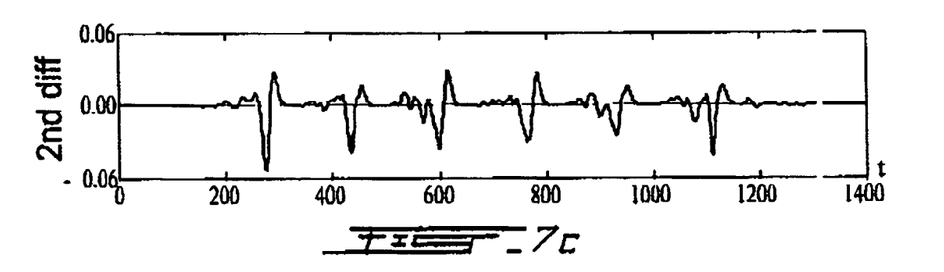
Figure 7D:
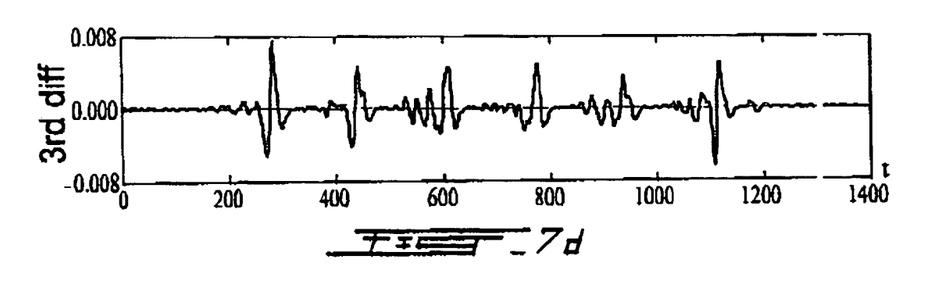
Figure 8A:
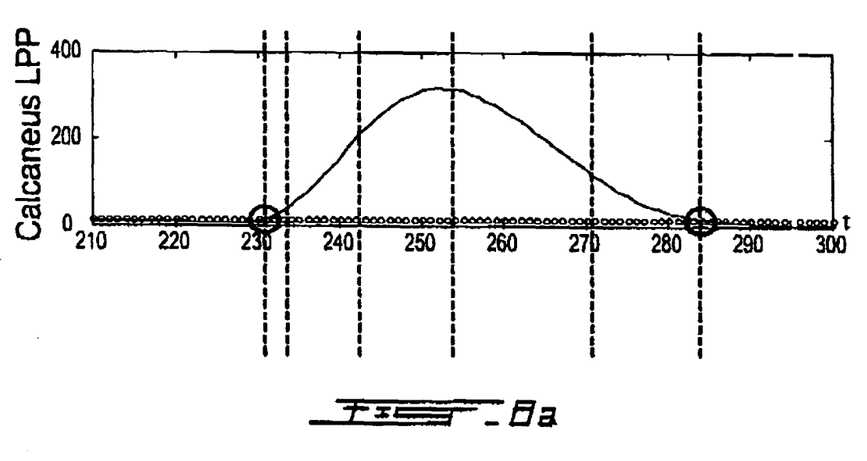
FIGS. 8a to 8d give an example of the zero crossings for a typical localized plantar pressure signal, and its first three differentials, at the calcaneus region conditions.
Figure 8B:
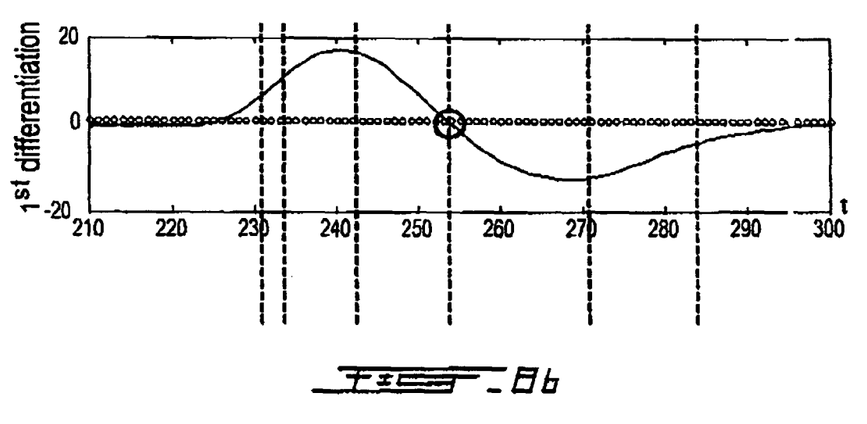
Figure 8C:
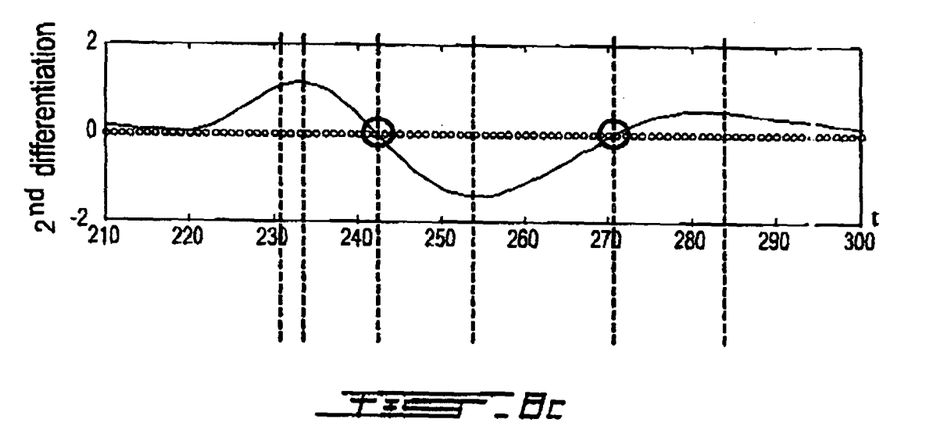
Figure 8D:
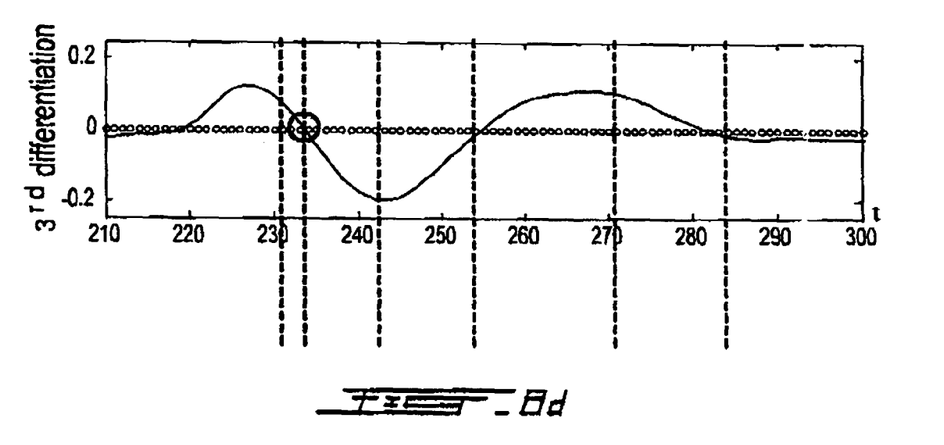

FIGS. 5a to 5d show examples of data signals from the four localized plantar pressure sensors (20) during a standard walking path at 109,5 steps/minute. The four signals, $f_{r1}(t)$, $f_{r2}(t)$, $f_{r3}(t)$ and $f_{r4}(t)$, correspond to the variation in time of the localized plantar pressure at the calcaneus region of the left foot (FIG. 5a), the MP region of the left foot (FIG. 5b), the calcaneus region of the right foot (FIG. 5c), and the MP region of the right foot (FIG. 5d).

FIGS. 6a to 6d and 7a to 7d show examples of graphs of localized plantar pressures, as well as their first, second and third differentials, at the calcaneus and MP regions respectively, for a linear walking path of 109,5 steps/minute.

Figure 9A:
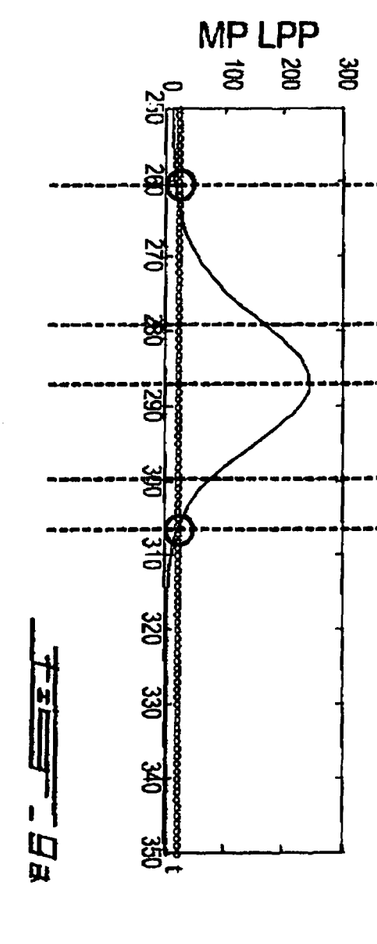
FIGS. 9a to 9c give an example of the zero crossings for a typical localized plantar pressure signal, and its first three differentials, at the metatarsophalangeal (MP) region.
Figure 9B:
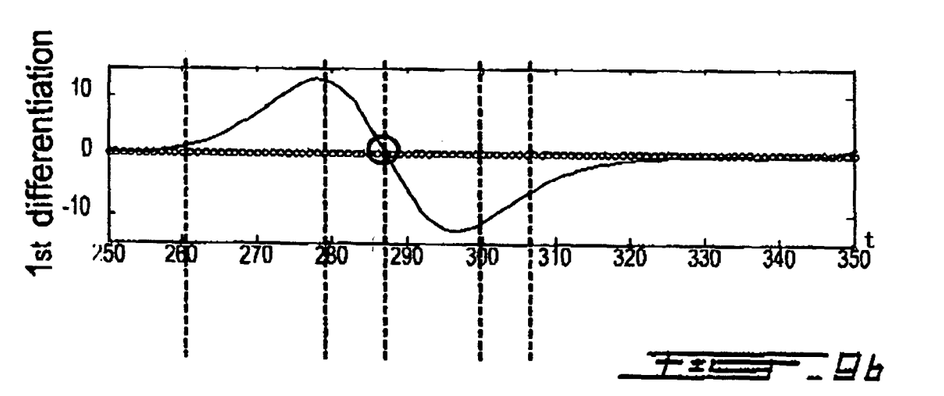
Figure 9C:
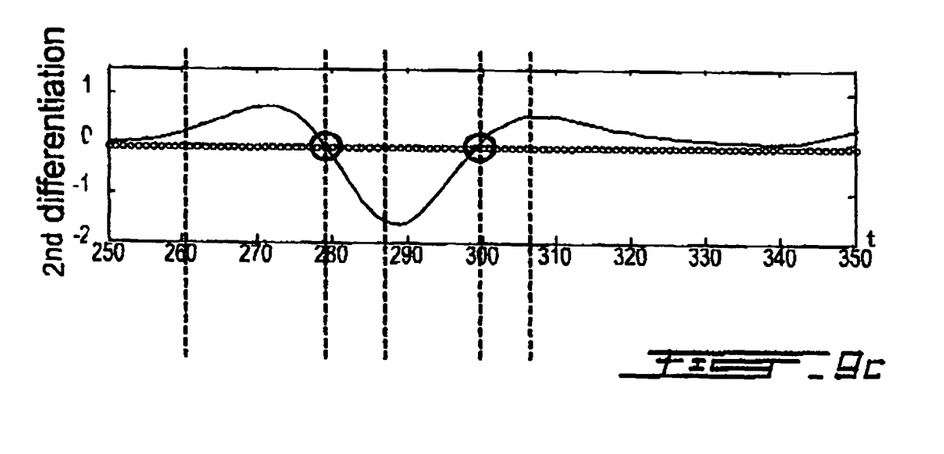

FIGS. 8a to 8d show graphically the zero crossings for a typical localized plantar pressure signal, and its first three differentials, at the calcaneous region conditions, which may be used by the controller (40) decompose The locomotion of the individual (10), while FIGS. 9a to 9c do so for the localized plantar pressure signal, and its first two differentials, at the MP region. This shows the relationships between the various data and derivative signals.

Accordingly, the controller (40) may use the four localized plantar pressure signals, the first, the second and the third differentials of each of those four localized plantar pressure signals, as well as the information gathered from the data signals of the two gyroscopes and the kinematic sensor, in order to decompose the locomotion of the individual (10) into a finite number of portions, and generate the controls signals for controlling the actuating mechanism (16) in response to the data signals. Of course, the controller (40) is not limited to the use of the preceding data and derived signals.

A controller (40) and control system (100) using artificial proprioceptors comprising plantar pressure sensors as well as gyroscopes and a kinematic sensor is described in U.S. patent application Ser. No. 10/600,725 filed Jun. 20, 2003, which is entitled "CONTROL SYSTEM AND METHOD FOR CONTROLLING AN ACTUATED PROSTHESIS", by Stéphane Bédard, the entire disclosure of which is hereby incorporated by reference herein.

What is claimed is:

1. A method of controlling an actuating mechanism of a prosthesis provided on one side of the lower body of an individual to provide coordinated movements, the individual having a healthy leg on the other side, the method comprising:

providing a plurality of artificial proprioceptors, at least one of the artificial proprioceptors being on the side of the healthy leg, and at least one of the artificial proprioceptors being provided with the prosthesis;

generating data signals in real time at the artificial proprioceptors, the data signals providing information about dynamics of locomotion of the individual;

decomposing the locomotion of the individual based on the information provided by the data signals from both the healthy leg and the prosthesis; and generating control signals in real time for controlling the actuating mechanism in response to the locomotion of the individual.

2. A method according to claim 1, wherein:
at least one of the data signals is supplied via a wired connection.

3. A method according to claim 1, wherein:
at least one of the data signals is supplied via a wireless connection.

4. A method according to claim 1, wherein:
the actuating mechanism is a passive electromechanical component that absorbs mechanical energy in order to modify dynamics of mechanical joints of the prosthesis.

5. A method according to claim 1, wherein:
the actuating mechanism is an active electro-mechanical component that absorbs and supplies mechanical energy in order to modify dynamics of mechanical joints of the prosthesis.

6. A method according to claim 1, wherein:
the artificial proprioceptors include myoelectric sensors.

7. A method according to claim 6, wherein:
the myoelectric sensors include external electrodes to measure myoelectric activity of skeletal muscles of the individual.

8. A method according to claim 6, wherein:
the myoelectric sensors include internal electrodes to measure myoelectric activity of skeletal muscles of the individual.

9. A method according to claim 1, wherein:
the artificial proprioceptors include neuro-sensors.

10. A method according to claim 9, wherein:
the neuro-sensors are electrodes to measure the summation of one or more action potentials of peripheral nerves of the individual.

11. A method according to claim 1, wherein:
the artificial proprioceptors include kinematic sensors.

12. A method according to claim 11, wherein:
the kinematic sensors include means for measuring the position of articulated joints of lower extremities parts of the individual.

13. A method according to claim 11, wherein:
the kinematic sensors include means for measuring the mobility speed of lower extremities parts of the individual.

14. A method according to claim 11, wherein:
the kinematic sensors include means for measuring the mobility acceleration of lower extremities parts of the individual.

15. A method according to claim 11, wherein:
at least one of the kinematic sensors is located at the shank of the healthy leg of the individual.

16. A method according to claim 11, wherein:
at least one of the kinematic sensors is located at a socket of the prosthesis.

17. A method according to claim 1, wherein:
the artificial proprioceptors include kinetic sensors.

18. A method according to claim 17, wherein:
the kinetic sensors include means for measuring rotational forces at articulated joints of lower extremities parts of the individual.

19. A method according to claim 17, wherein:
the kinetic sensors include means for measuring reaction forces at lower extremities parts of the individual.

20. A method according to claim 17, wherein:
at least one of the kinetic sensors is located at a transtibial post of the prosthesis.

21. A method according to claim 1, wherein:
the artificial proprioceptors include plantar pressure sensors.

22. A method according to claim 21, wherein:
the plantar pressure sensors include force-sensing resistors measuring the pressure forces at underfoot areas into at least one human body plan.

23. A method according to claim 21, wherein:
at least one of the plantar pressure sensors is located at a metatarsophalangeal region of a foot of the healthy leg; and
at least one of the plantar pressure sensors is located at a calcaneus region of the foot of the healthy leg.

24. A method according to claim 21, wherein:
at least one of the plantar pressure sensors is located at a metatarsophalangeal region of a prosthetic foot of the prosthesis; and
at least one of the plantar pressure sensors is located at a calcaneus region of the prosthetic foot of the prosthesis.

25. A device for controlling an actuating mechanism of a prosthesis provided on one side of the lower body of an individual to provide coordinated movements, the individual having a healthy leg on the other side, the device comprising:
a plurality of artificial proprioceptors, at least one of the artificial proprioceptors being configured to be positioned on the side of the healthy leg, and at least one of the artificial proprioceptors being configured to be positioned on the side of the prosthesis;
means for generating data signals in real time at the artificial proprioceptors, the data signals providing information about dynamics of locomotion of the individual;
means for decomposing the locomotion of the individual based on the information provided by the data signals from both the healthy leg and the prosthesis; and
means for generating control signals in real time for controlling the actuating mechanism in response to the locomotion of the individual.

26. A device according to claim 25, wherein:
at least one of the data signals is supplied via a wired connection.

27. A device according to claim 25, wherein:
at least one of the data signals is supplied via a wireless connection.

28. A device according to claim 25, wherein:
the actuating mechanism is a passive electromechanical component that absorbs mechanical energy in order to modify dynamics of mechanical joints of the prosthesis.

29. A device according to claim 25, wherein:
the actuating mechanism is an active electro-mechanical component that absorbs and supplies mechanical energy in order to modify dynamics of mechanical joints of the prosthesis.

30. A device according to claim 25, wherein:
the artificial proprioceptors include myoelectric sensors.

31. A device according to claim 30, wherein:
the myoelectric sensors include external electrodes to measure myoelectric activity of skeletal muscles of the individual.

32. A device according to claim 30, wherein:
the myoelectric sensors include internal electrodes to measure myoelectric activity of skeletal muscles of the individual.

33. A device according to claim 25, wherein:
the artificial proprioceptors include neuro-sensors.

34. A device according to claim 33, wherein:
the neuro-sensors are electrodes to measure the summation of one or more action potentials of peripheral nerves of the individual.

35. A device according to claim 25, wherein:
the artificial proprioceptors include kinematic sensors.

36. A device according to claim 35, wherein:
the kinematic sensors include means for measuring the position of articulated joints of lower extremities parts of the individual.

37. A device according to claim 35, wherein:
the kinematic sensors include means for measuring the mobility speed of lower extremities parts of the individual.

38. A device according to claim 35, wherein:
the kinematic sensors include means for measuring the mobility acceleration of lower extremities parts of the individual.

39. A device according to claim 35, wherein:
at least one of the kinematic sensors is located at the shank of the healthy leg of the individual.

40. A device according to claim 35, wherein:
at least one of the kinematic sensors is located at a socket of the prosthesis.

41. A device according to claim 25, wherein:
the artificial proprioceptors include kinetic sensors.

42. A device according to claim 41, wherein:
the kinetic sensors include means for measuring rotational forces at articulated joints of lower extremities parts of the individual.

43. A device according to claim 41, wherein:
the kinetic sensors include means for measuring reaction forces at lower extremities parts of the individual.

44. A device according to claim 41, wherein:
at least one of the kinetic sensors is located at a transtibial post of the prosthesis.

45. A device according to claim 25, wherein:
the artificial proprioceptors include plantar pressure sensors.

46. A device according to claim 45, wherein:
the plantar pressure sensors include force-sensing resistors measuring the pressure forces at underfoot areas into at least one human body plan.

47. A device according to claim 45, wherein:
at least one of the plantar pressure sensors is located at a metatarsophalangeal region of a foot of the healthy leg; and
at least one of the plantar pressure sensors is located at a calcaneus region of the foot of the healthy leg.

48. A device according to claim 45, wherein:
at least one of the plantar pressure sensors is located at a metatarsophalangeal region of a prosthetic foot of the prosthesis; and
at least one of the plantar pressure sensors is located at a calcaneus region of the prosthetic foot of the prosthesis.

49. A lower extremities prosthesis configured to be provided on one side of the lower body of an individual to provide coordinated movements, the individual having a healthy leg on the other side, the prosthesis comprising:
a plurality of artificial proprioceptors, at least one of the artificial proprioceptors being configured to be positioned on the side of the healthy leg, and at least one of the artificial proprioceptors being provided with the prosthesis;
means for generating data signals in real time at the artificial proprioceptors, the data signals providing information about dynamics of locomotion of the individual;
means for decomposing the locomotion of the individual based on the information provided by the data signals from both the healthy leg and the prosthesis;
at least one actuating mechanism; and
means for generating control signals in real time for controlling the actuating mechanism in response to the locomotion of the individual.

50. A prosthesis according to claim 49, wherein:
at least one of the data signals is supplied via a wired connection.

51. A prosthesis according to claim 49, wherein:
at least one of the data signals is supplied via a wireless connection.

52. A prosthesis according to claim 49, wherein:
the actuating mechanism is a passive electromechanical component that absorbs mechanical energy in order to modify dynamics of mechanical joints of the prosthesis.

53. A prosthesis according to claim 49, wherein:
the actuating mechanism is an active electromechanical component that absorbs and supplies mechanical energy in order to modify dynamics of mechanical joints of the prosthesis.

54. A prosthesis according to claim 49, wherein:
the artificial proprioceptors include myoelectric sensors.

55. A prosthesis according to claim 54, wherein:
the myoelectric sensors include external electrodes to measure myoelectric activity of skeletal muscles of the individual.

56. A prosthesis according to claim 54, wherein:
the myoelectric sensors include internal electrodes to measure myoelectric activity of skeletal muscles of the individual.

57. A prosthesis according to claim 49, wherein:
the artificial proprioceptors include neuro-sensors.

58. A prosthesis according to claim 57, wherein:
the neuro-sensors are electrodes to measure the summation of one or more action potentials of peripheral nerves of the individual.

59. A prosthesis according to claim 49, wherein:
the artificial proprioceptors include kinematic sensors.

60. A prosthesis according to claim 59, wherein:
the kinematic sensors include means for measuring the position of articulated joints of lower extremities parts of the individual.

61. A prosthesis according to claim 59, wherein:
the kinematic sensors include means for measuring the mobility speed of lower extremities parts of the individual.

62. A prosthesis according to claim 59, wherein:
the kinematic sensors include means for measuring the mobility acceleration of lower extremities parts of the individual.

63. A prosthesis according to claim 59, wherein:
at least one of the kinematic sensors is located at the shank of the healthy leg of the individual.

64. A prosthesis according to claim 59, wherein:
at least one of the kinematic sensors is located at a socket of the prosthesis.

65. A prosthesis according to claim 49, wherein:
the artificial proprioceptors include kinetic sensors.

66. A prosthesis according to claim 65, wherein:
the kinetic sensors include means for measuring rotational forces at articulated joints of lower extremities parts of the individual.

67. A prosthesis according to claim 65, wherein:
the kinetic sensors include means for measuring reaction forces at lower extremities parts of the individual.

68. A prosthesis according to claim 65, wherein:
at least one of the kinetic sensors is located at a transtibial post of the prosthesis.

69. A prosthesis according to claim 49, wherein:
the artificial proprioceptors include plantar pressure sensors.

70. A prosthesis according to claim 69, wherein:
the plantar pressure sensors include force-sensing resistors measuring the pressure forces at underfoot areas into at least one human body plan.

71. A prosthesis according to claim 69, wherein:
at least one of the plantar pressure sensors is located at a metatarsophalangeal region of a foot of the healthy leg; and
at least one of the plantar pressure sensors is located at a calcaneus region of the foot of the healthy leg.

72. A prosthesis according to claim 69, wherein:
at least one of the plantar pressure sensors is located at a metatarsophalangeal region of a prosthetic foot of the prosthesis; and
at least one of the plantar pressure sensors is located at a calcaneus region of the prosthetic foot of the prosthesis.

73. A method according to claim 4, wherein:
the control signals include a resistance to be applied by the passive electromechanical component to the mechanical joints of the prosthesis.

74. A method according to claim 5, wherein:
the control signals include joint trajectories and torque to be applied by the active electro-mechanical component to the mechanical joints of the prosthesis.

75. A device according to claim 28, wherein:

the control signals include a resistance to be applied by the passive electromechanical component to the mechanical joints of the prosthesis.

76. A device according to claim 29, wherein:

the control signals include joint trajectories and torque to be applied by the active electro-mechanical component to the mechanical joints of the prosthesis.

77. A prosthesis according to claim 52, wherein:

the control signals include a resistance to be applied by the passive electromechanical component to the mechanical joints of the prosthesis.

78. A prosthesis according to claim 53, wherein:

the control signals include joint trajectories and torque to be applied by the active electro-mechanical component to the mechanical joints of the prosthesis.

\* \* \* \* \*

UNITED STATES PATENT AND TRADEMARK OFFICE
CERTIFICATE OF CORRECTION

PATENT NO. : 7,137,998 B2  Page 1 of 1
APPLICATION NO. : 10/627503
DATED : November 21, 2006
INVENTOR(S) : Stephane Bedard It is certified that error appears in the above-identified patent and that said Letters Patent is hereby corrected as shown below:

On the title page, item(73), insert --Assignee: Victhom Human Bionics Inc Saint-Augustin-De-Desmaures (CA)--

Signed and Sealed this

Third Day of April, 2007

JON W. DUDAS
*Director of the United States Patent and Trademark Office*